United States Patent [19]

Proctor et al.

[11] Patent Number: 4,498,782
[45] Date of Patent: Feb. 12, 1985

[54] ASSEMBLY FOR DETERMINING LIGHT TRANSMISSIVENESS OF A FLUID

[75] Inventors: David R. Proctor; Terry L. Foster, both of Abilene, Tex.

[73] Assignee: Science Research Center, Inc., Abilene, Tex.

[21] Appl. No.: 268,167

[22] Filed: May 29, 1981

[51] Int. Cl.³ ............................................. G01N 21/27
[52] U.S. Cl. ..................... 356/436; 356/440
[58] Field of Search ............... 356/246, 440, 244, 432, 356/435; 250/373, 575, 576

[56] References Cited

U.S. PATENT DOCUMENTS

| | | | |
|---|---|---|---|
| 3,773,426 | 11/1973 | Mudd | 356/246 |
| 3,847,482 | 11/1974 | Sokol et al. | 356/244 |
| 4,004,150 | 1/1977 | Natelson | 250/373 |
| 4,037,972 | 7/1977 | Pross | 356/435 |
| 4,115,010 | 9/1978 | McAleer et al. | 356/440 |
| 4,171,909 | 10/1979 | Kramer et al. | 356/435 |
| 4,240,751 | 12/1980 | Linnecke et al. | 356/246 |
| 4,310,249 | 1/1982 | Kramer | 356/432 |

FOREIGN PATENT DOCUMENTS 2729684 3/1978 Fed. Rep. of Germany ...... 356/432

Primary Examiner—R. A. Rosenberger
Attorney, Agent, or Firm—Kane, Dalsimer, Kane, Sullivan and Kurucz

[57] ABSTRACT

The disclosure is of an assembly for determining light transmissiveness of a fluid. The assembly comprises a light source, means of holding the fluid in a light-shielded path of the light generated and a means for receiving and measuring the attenuated light passed through the fluid sample. The assembly is simple and highly portable. As such it is convenient for use with little training in places such as a physician's office, for measuring substances in immunoassay reaction mixtures.

6 Claims, 9 Drawing Figures

ASSEMBLY FOR DETERMINING LIGHT TRANSMISSIVENESS OF A FLUID

BACKGROUND OF THE INVENTION

1. Field of the Invention

The invention relates to the detection and measurement of substances present in a fluid and more particularly relates to those methods and apparatus based upon the light transmissiveness of the fluid.

2. Brief Description of the Prior Art

The prior art literature is replete with descriptions of methods and apparatus for the detection and measurement of substances present in fluids. Representative of descriptions found in the prior art are those found in U.S. Pat. Nos. 3,773,426 and 4,240,751.

In spite of the number of prior art methods and apparatus for detecting and measuring substances present in fluids by determining the light transmissiveness of the fluid, there remains a need for improved apparatus. In particular, there has been a need for highly portable, simple apparatus which can be operated with a minimum of instruction and training.

The assembly of the present invention is compact, simple in design, highly portable and easy to operate. In spite of its simplicity, the assemblies of the invention are accurate and highly reliable in operation.

SUMMARY OF THE INVENTION

The invention comprises an assembly for determining the light transmissiveness of a fluid contained in a light-transparent well of a microtiter plate, which comprises:

1. a light reception component, which comprises;
    (a) a light-shield adapted by size and configuration to receive the well portion of the microtiter plate and to prevent the passage of light through the sidewalls and the bottom of said well portion;
    (b) an aperture in the light-shield, having an entry and an exit;
    (c) light-conducting means having a first end and a second end, the first end being associated with the exit of said aperture whereby light passing out of the exit is received and conducted to the second end of said means;
    (d) a photo-detector cell mounted to receive light from the second end of the light-conducting means and to generate an electrical signal proportional to the light intensity; and
    (e) means in electrical connection with the photo-detector cell for receiving and converting the signal to visually observable indicia; and
2. a light transmission component which comprises:
    (a) a light source;
    (b) a housing for the light source; and
    (c) an aperture in the housing, for passage of light out of the housing;

said light transmission component being adapted to pass light through the well of a microtiter plate shielded by said light shield, and into the entry of the aperture 1.(b).

The assembly of the invention is particularly useful in determining the presence of biological substances in aqueous mixtures, such as for example immunological reactants in immunoassay reaction mixtures.

DETAILED DESCRIPTION OF THE PREFERRED EMBODIMENTS OF THE INVENTION

Figure 1:
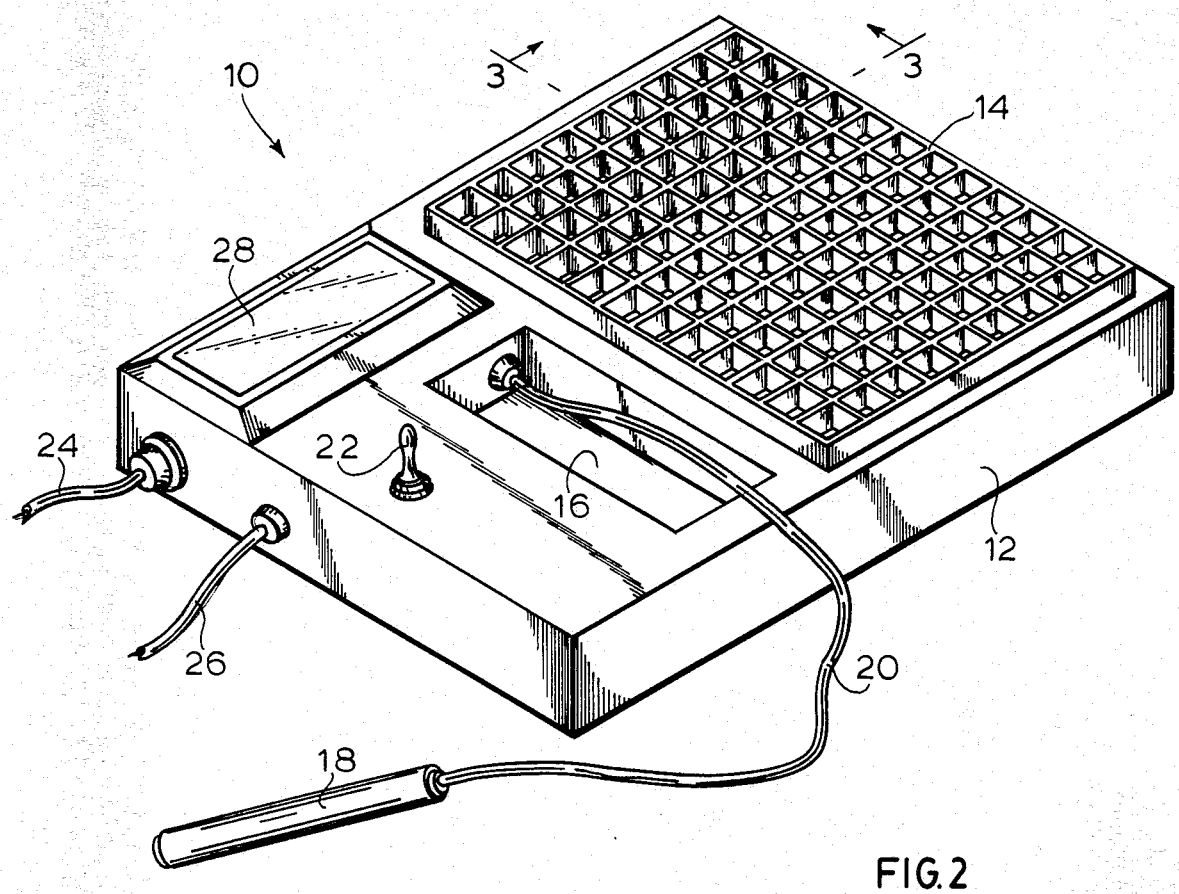
FIG. 1 is a view-in-perspective of an embodiment assembly of the invention.

FIG. 1 is a view-in-perspective of a preferred embodiment assembly 10 of the invention. The assembly 10 comprises a housing 12 having integrally formed on a portion of its upper surface a light-shield means 14, which will be described in greater detail hereinafter. The housing 12 may be fabricated from any conventional material such as metal or it may be molded from a synthetic polymeric resin such as polystyrene, polycarbonate, polyurethane and the like. The housing 12 includes a recess 16 adapted to receive and hold a light wand 18 which is attached by power cord 20 to a power source (not shown in FIG. 1). An electrical switch 22 is electrically connected to the power cord 20 and the power source as a means for energizing and deenergizing the light wand 18. A power cord 24, connected to a conventional power source (not shown), is also electrically connected with switch 22 and through switch 22 to the power cord 20 so that a continuous electrical current may be controlled through switch 22, to the light wand 18. Exiting the housing 12 is an electrical cable 26 which may link the assembly 10 to, for example, ancillary equipment such as a computer or like recording device. The cable 26 is connected within housing 12 with electrical means for converting the electrical signal from a photo detector, as will be described more completely hereinafter. On the upper surface of the housing 12 there is also a display member 28 for visually indicating observable indicia generated by the electrical signal as will also be described more fully hereinafter.

Figure 2:
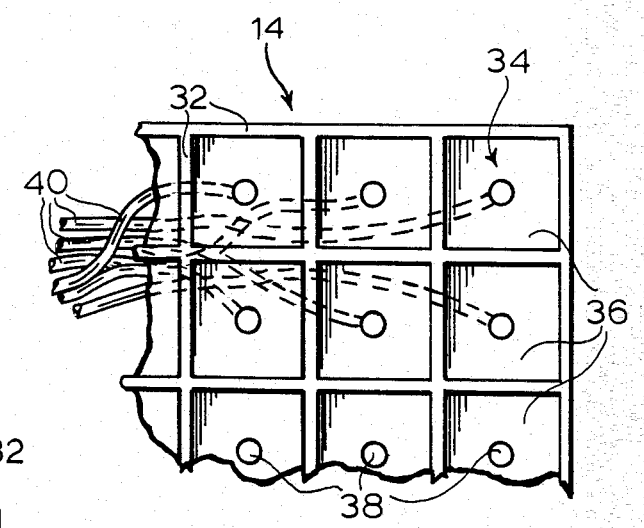
FIG. 2 is a top view of a portion of the assembly shown in FIG. 1.

FIG. 2 is an enlarged, top view of a portion of the light shield component 14 shown in FIG. 1. It will be observed from the FIG. 2 that the light shield 14 is made up of intersecting light-proof walls 32 defining a well or recess 34 having a light-proof bottom 36. The recess 34 is adapted by size and configuration to receive the well, including its sidewalls and bottom wall, of a conventional microtiter plate and to prevent the passage of light beyond the sidewalls and the bottom of the well in the microtiter plate.

Microtiter plates are commercially available from, for example, Cooke Laboratory Products Division, Dynatech Labs. Inc., Alexandria, Va. Although the plate shown in the accompanying drawings has a square-shaped well, others may be spherical, cylindrical, or of other shapes. There is an aperture 38 in the bottom 36 of the individual recesses 34 of the light-shield 14. The entrance to aperture 38 is from recess 34 and the exit is within the housing 12 as seen best in FIG.

3, a view along lines 3—3 of FIG. 1 with an inserted microtiter plate 15 of conventional manufacture.

Figure 3:
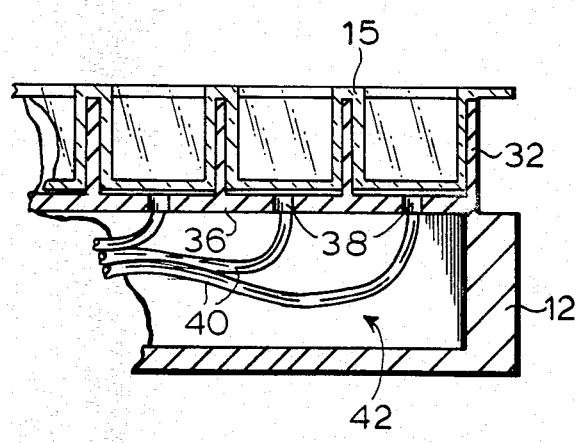
FIG. 3 is a view along lines 3—3 of FIG. 1 after insertion of a conventional microtiter plate.

FIG. 3 shows that the well portions of the microtiter plate 15, when inserted in light-shield 14, are completely surrounded by the walls 32 and bottom 36 of the light-shield 14, leaving the entrance to the well open to light. FIG. 3 also shows that the exit portion of the aperture 38 receives and is connected to a strand of fiber optic 40 which traverses the interior chamber 42 of housing 12. Fiber optic 40 is a means of conducting light from a first end thereof at the exit of aperture 38 to a second end (not shown in FIGS. 2 and 3). It will be appreciated that light passing into the open top of the microtiter 15 wells will pass through the well and into the entrance of aperture 38 without loss through the shielded sidewalls and bottom.

Figure 4:
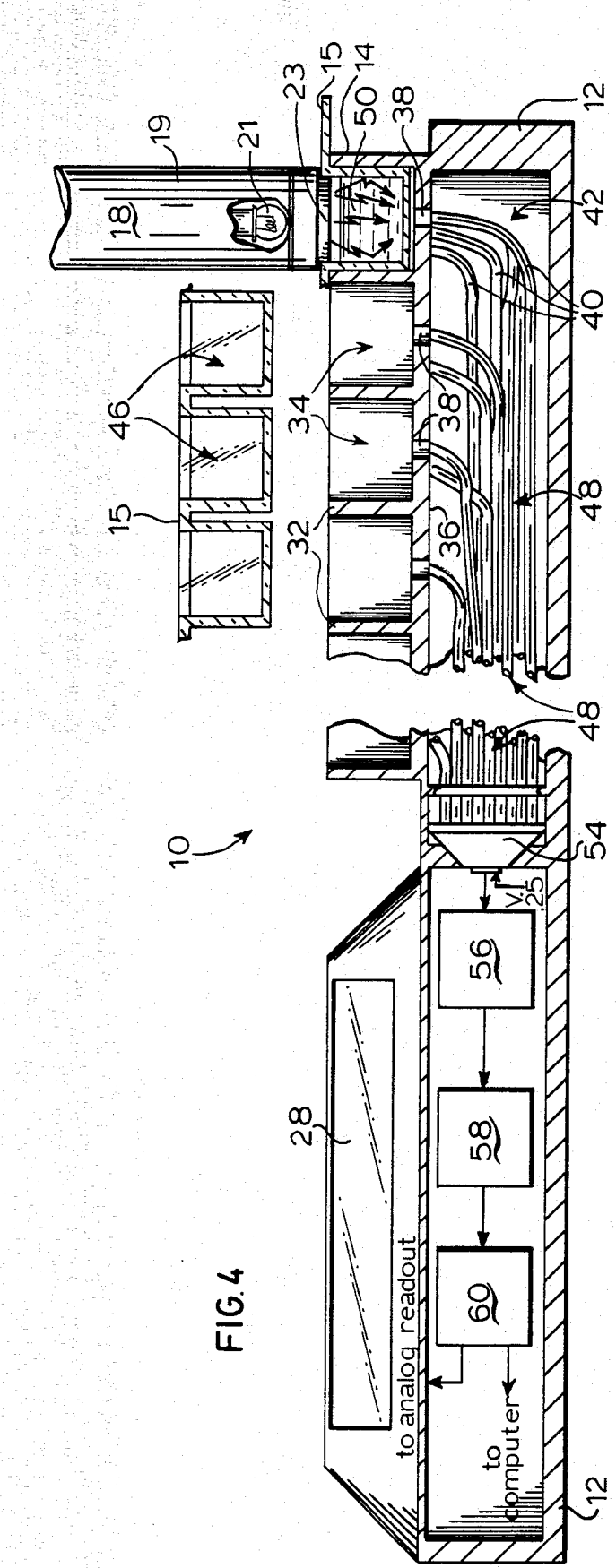
FIG. 4 is a cross-sectional side elevation (fragmented) of the embodiment assembly shown in FIG. 1.
Figure 5:
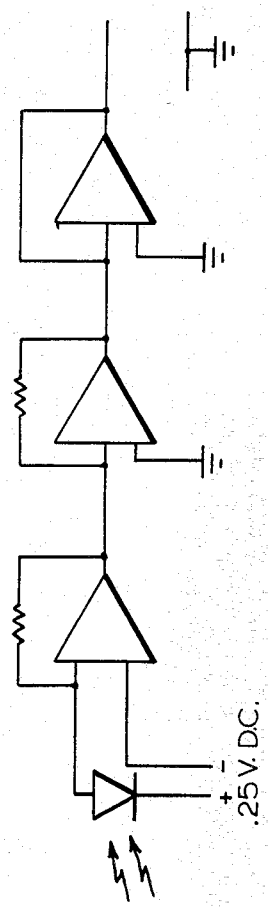
FIG. 5 is a schematic drawing of an embodiment electrical circuit found in the assembly of FIG. 4.

FIG. 4 is a side elevation of the assembly 10, fragmented, showing further details of the assembly 10. In the right hand side of the drawing, it may be seen that the strands of fiber optics 40 from each individual aperture 38 come together and are held together in a fiber bundle 48. The bundle 48 of fiber optics is positioned so that the free ends of fiber optics 40 distal to the ends associated with the aperture 38 are aligned adjacent to and in association with a photo-detector cell 54. As shown in the right hand side of FIG. 4, the light wand 18 which comprises a tubular housing 19 containing a low voltage photo-bulb 21 and an apertured end 23 has been energized and positioned over the opening 46 of a microtiter plate 15 inserted in the light-shield 14. The well beneath light wand 18 contains a fluid 50 having in admixture a biological substance for detection and measurement. When the light wand 18 is activated, incident light is transmitted from bulb 21 and directed through the apertured end 23 into fluid 50. The light continues through the fluid 50 and a portion thereof passes through aperture 38 to the fiber optic 40. The transmitted light is conducted by fiber optic 40 to the photo-detector cell 54. The photo-detector cell 54 converts the conducted light, in proportion to its intensity, to an electrical signal. This electrical signal may be amplified in a pair of amplifiers 56, 58 and then through a buffer circuit or amplifier 60. The amplified signal is then carried by electrical wire to a means 28 for receiving and converting the amplified signal to a visually observable indicia, such as for example, a volt meter, analog readout, digital readout or like ancillary components. The schematic electrical diagram for the above described electrical circuit from the photo-detector cell 54 is shown in FIG. 5 and operates on an initial voltage of 0.25 volts (D.C.). The voltage can be boosted to any desired output by selection of amplifiers 56, 58.

In summary, incident light shining through the various fluids in the test wells of a conventional microtiter plate 15 energize the photo-detector cell 54 to cause current flow in the circuitry of FIG. 5. In operation, a test determination is made upon a sample fluid by first calibrating the assembly 10 by having light from the wand 18 pass through a calibrating fluid such as distilled water. Then, when an actual test is performed upon an unknown fluid, the light passing through the test fluid is attenuated. The degree of attenuation causes light of a lesser intensity to impinge on the photo-detector cell 54 with a corresponding reduction in current flow. This reduction in current flow is measurable by means 28 for visible indicia and serves as a measure of the amount of unknown substance contained within the fluid 50. Known samples can also be used to calibrate and measure test specimens as will be appreciated by those skilled in the art.

Figure 6:
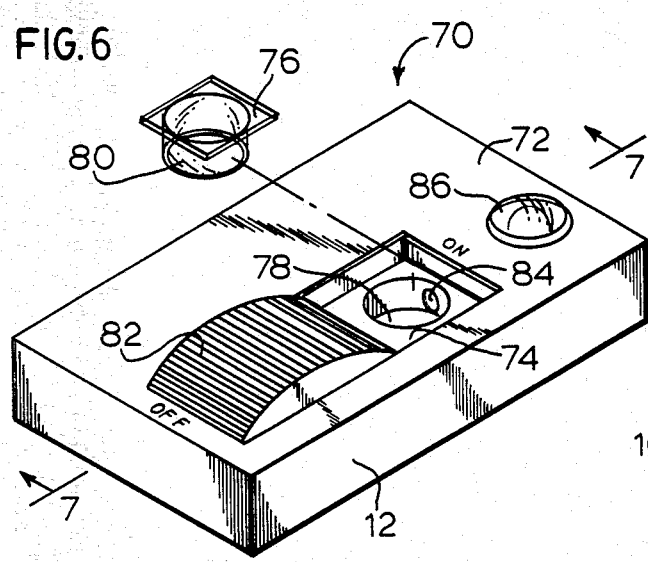
FIG. 6 is a view-in-perspective of another embodiment assembly of the invention.
Figure 7:
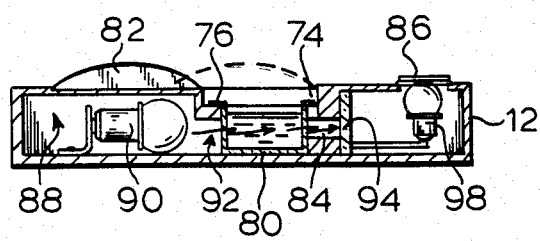
FIG. 7 is a cross-sectional, side elevation along lines 7—7 of FIG. 6.

FIG. 6 shows another embodiment assembly 70 of the invention which comprises a highly portable, hand holdable housing 72 within which there is a recess 74 for receiving a single well microtiter plate 76. The bottom of recess 74 has a well 78, cylindrical in shape, for receiving the lower well portion 80 of microtiter plate 76 whereby the well portion 80 of microtiter plate 76 is shielded from ingress or egress of light through the sidewalls or bottom. A slidable cover 82 will close recess 74 and make it light-proof when the microtiter plate 76 containing a fluid for analysis is inserted therein. With the slidable cover 82 closed, the microtiter plate 76 is completely shielded from outside light or escaping light. Aperture 84 in the sidewall of well 78 permits the passage of light passing from the transparent sidewall of well 80 of microtiter plate 76; see FIG. 7, a view along lines 7—7 of FIG. 6. As shown in FIG. 7, the interior chamber 88 of housing 12 contains a source of incident light in low-voltage (6 volt) photo-bulb 90 which is connected to a power source (not shown) and energized by the closing of cover 82 (which alternately functions as an electrical switch). When the switch is closed to initiate light from bulb 90, the light passes through light pathway 92 (a light-conducting means), a fluid contained within the well 80 and through aperture 84 to impinge upon a photo-detector cell 94. Photo-detector cell 94, converts the attenuated light energy as described above in relation to embodiment assembly 10, into electrical current to activate bulb 98, thereby giving a visual signal through window 86. Although not shown in FIG. 7, the same circuitry used in FIG. 5 may be employed to amplify the output electrical signal from photo-detector cell 94 when desired.

Figure 8:
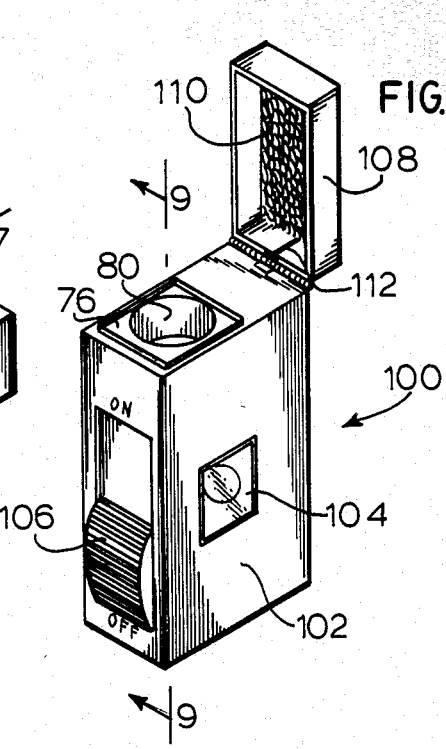
FIG. 8 is a view-in-perspective of still another embodiment assembly of the invention.

FIG. 8 shows still another embodiment assembly 100 of the invention which includes a housing 102 which is highly portable and hand holdable. A window 104 is in the side of housing 102. The microtiter plate 76 sits on the upper surface of housing 102 within a recess (not shown in FIG. 8). A closable lid 108 contains in its end wall a photo-detector cell 110. When lid 108 is closed over plate 76, electrical connector 112 is closed to join the photo-detector cell 110 in electrical connection with a circuit such as that shown in FIG. 5, and which may be positioned within housing 102 (not shown in position).

Figure 9:
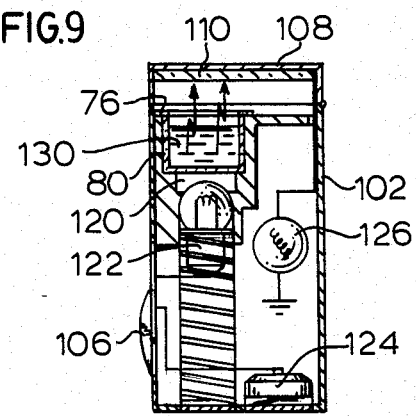
FIG. 9 is a view along lines 9—9 of FIG. 8.

Referring now to FIG. 9, a view along lines 9—9 of FIG. 8 one may see some of the internal components of the assembly 100. In the assembly 100, when a microtiter plate 76 is inserted within the recess and lid 108 closed to make a light-proof containment, an electrical switch 106 may be closed to energize low-voltage photo-bulb 122. Bulb 122 as an incident light source sends light through channel 120 (a means of conducting light), on through the fluid contained in microtiter plate 76 and across to strike the photo-detector cell 110. Photo-detector cell 110, converts the light energy in direct proportion to its intensity to an electrical signal which is transmitted to a light-emitting diode 126 for visual readout through the window 104. Battery 124 supplies the electric energy to energize the bulb 122.

The assemblies of the invention 70 and 100 may be set to indicate only when certain minimum proportions of biological substances are present within the fluid being analyzed by selection of the sensitivity of the photo-detector cell. Thus, they do not require comparative, digital readouts but merely provide a signal of certain levels or concentrations of substance within the fluid being analyzed.

The simple, readily operated and highly portable embodiment assemblies of FIGS. 6-9 are particularly useful, for example, in a physician's office as an instrument to screen patients for immunological characteristics. For example, if a physician desired to screen a patient for possible IgG presence in the blood he would place some of the patient's blood serum in a microtiter plate with anit-IgG. If there occurs an antibody/antigen reaction, the immunological precipitate may be detected by an increased attenuation of light transmitted through the reaction mixture. By selection of a photo-detector cell which will detect a particular level of light transmissiveness associated with a positive immunological reaction mixture, but not a higher degree of transmissiveness (associated with a negative reaction) one can design the assemblies of the invention to provide a visible indicia (signal light 98 or 126 being energized) when the test indicates an immunological reaction occurred. Thus, the embodiment assemblies of FIGS. 6-9 are qualitative, screening devices.

Those skilled in the art will appreciate that many modifications may be made to the preferred embodiments described above without departing from the spirit and the scope of the invention. For example, when desired one may include a variety of light filters such as interference filters in the light pathways described above to employ only certain wavelengths of light for the measurement of transmissiveness of particular fluid mixtures. A lens may also be included in light pathways for columnating the light and focusing it on collecting components. Power sources do not form a part of the invention and may be A.C. or D.C. sources including battery (rechargeable or disposable) sources.

We claim:

1. An assembly for determining the light transmissiveness of a fluid contained in a light-transparent well of a microtiter plate, wherein there are a plurality of wells in the microtiter plate, which comprises:
   1. a light reception component, which comprises:
      (a) a light-shield adapted by size and configuration to receive the multiple well portion of the microtiter plate and the light-shield receives each well;
      (b) a plurality of apertures in the light-shield, each aperture having an entry and an exit into one of each wells;
      (c) a plurality of light-conducting means, each having a first and second end, the first end being associated with an exit of one of said apertures whereby light passing out of each exit is separately received and conducted to the second end of each of said means;
      (d) a photo-detector cell mounted to receive light from the second ends of each light-conducting means and to generate an electrical signal proportional to the light intensity; and
      (e) means in electrical connection with the photo-detector cell for receiving and converting the signal to visually observable indicia; and
   2. a light transmission component, which comprises;
      (a) a light source;
      (b) a housing for the light source; and
      (c) an aperture in the housing, for passage of light out of the housing; said light transmission component being adapted to pass light separately through each well of a microtiter plate shielded by said light-shield, and separately into each entry of each aperture 1. (b).

2. The assembly of claim 1 wherein the light-conducting means 1. (c) comprises a fiber optic.

3. The assembly of claim 2 which further comprises an amplifier for amplifying said signal.

4. The assembly of claim 2 which further comprises a housing for holding the components (1.).

5. The assembly of claim 2 wherein said means for converting the signal to visually observable indicia comprises an analog readout.

6. The assembly of claim 2 which is hand holdable and portable.

* * * * *